United States Patent
Makarov et al.

(10) Patent No.: US 11,723,796 B2
(45) Date of Patent: *Aug. 15, 2023

(54) SYSTEM AND METHOD FOR COOLING OR HEATING A HUMAN BODY PART

(71) Applicant: TecTraum, Inc., Chagrin Falls, OH (US)

(72) Inventors: Sergey Makarov, Solon, OH (US); Jason R. Ertel, Twinsburg, OH (US); David J. Boll, Avon, OH (US)

(73) Assignee: TECTRAUM, INC., Chagrin Falls, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/551,528

(22) Filed: Dec. 15, 2021

(65) Prior Publication Data

US 2022/0104966 A1  Apr. 7, 2022

Related U.S. Application Data

(63) Continuation of application No. 15/934,201, filed on Mar. 23, 2018, now Pat. No. 11,229,547.

(51) Int. Cl.
*A61F 7/02* (2006.01)
*A61F 7/00* (2006.01)
*A61B 17/00* (2006.01)

(52) U.S. Cl.
CPC ...... *A61F 7/02* (2013.01); *A61B 2017/00084* (2013.01); *A61F 2007/0001* (2013.01);
(Continued)

(58) Field of Classification Search
CPC ...... A61F 2007/0054; A61F 2007/0056; A61F 7/0085
See application file for complete search history.

(56) References Cited

U.S. PATENT DOCUMENTS 4,844,072 A * 7/1989 French ............... A61F 7/02
219/535
5,484,448 A   1/1996 Steele
(Continued)

FOREIGN PATENT DOCUMENTS

CN  102837689  12/2012
CN  104024564  9/2014
(Continued)

OTHER PUBLICATIONS

Cole-Parmer Blog Team, Why Centrifugal Pumps Dominate the Market Video, Jan. 12, 2015 (Year: 2015).*
(Continued)

*Primary Examiner* — Kaitlyn E Smith
(74) *Attorney, Agent, or Firm* — Rankin, Hill & Clark LLP

(57) ABSTRACT

A system for cooling or heating a body part includes at least one bladder, a pump, a heat exchanger, a first fluid line in fluid communication with the heat exchanger and the at least one bladder, a second fluid line in fluid communication with the at least one bladder and the heat exchanger, a main reservoir and a separator. The heat exchanger is in fluid communication with the pump. The first fluid line is located downstream from the heat exchanger and the second fluid line is located downstream from the at least one bladder when the system is operating to cool or heat the body part. The separator is in fluid communication with the main reservoir and the pump and is located below the main reservoir to receive fluid under the influence of gravity from the main reservoir and to deliver fluid to the pump via gravity.

16 Claims, 2 Drawing Sheets

(52) U.S. Cl.
CPC ........... *A61F 2007/0056* (2013.01); *A61F 2007/0096* (2013.01); *A61F 2007/0225* (2013.01)

(56) References Cited

U.S. PATENT DOCUMENTS

| | | | |
|---|---|---|---|
| 5,755,755 | A | 5/1998 | Panyard |
| 6,156,059 | A | 12/2000 | Olofsson |
| 6,183,501 | B1 | 2/2001 | Latham |
| 6,312,453 | B1 | 11/2001 | Stefanile |
| 6,511,502 | B2 | 1/2003 | Fletcher |
| 7,846,118 | B2 | 12/2010 | Sandhu |
| 7,896,910 | B2 | 3/2011 | Schirrmacher |
| 8,425,583 | B2 | 4/2013 | Nofzinger |
| 8,454,671 | B2 | 6/2013 | Lennox |
| 8,900,170 | B1 | 12/2014 | Elkins |
| 11,229,547 | B2 * | 1/2022 | Makarov ............... A61F 7/02 |
| 2003/0114903 | A1 * | 6/2003 | Ellingboe ............ A61F 7/0085 607/104 |
| 2005/0065584 | A1 | 3/2005 | Schiff |
| 2005/0096714 | A1 * | 5/2005 | Freedman ............. A61F 7/00 607/104 |
| 2008/0097561 | A1 | 4/2008 | Melsky |
| 2010/0137951 | A1 | 6/2010 | Lennox |
| 2011/0295163 | A1 | 12/2011 | Vijayanagar |
| 2012/0288848 | A1 | 11/2012 | Latham et al. |
| 2013/0138185 | A1 | 5/2013 | Paxman |
| 2014/0046411 | A1 | 2/2014 | Elkins |
| 2014/0277302 | A1 | 9/2014 | Weber |
| 2014/0343639 | A1 * | 11/2014 | Hopper ............... A61F 7/0085 607/104 |
| 2015/0352314 | A1 | 12/2015 | Walker |
| 2016/0022477 | A1 | 1/2016 | Schaefer |
| 2016/0354232 | A1 | 12/2016 | Rozental |

FOREIGN PATENT DOCUMENTS

| | | |
|---|---|---|
| CN | 107060002 | 8/2017 |
| WO | 2012028730 | 3/2012 |

OTHER PUBLICATIONS

Supplementary EP Search Report filed in EP 19772031 dated Nov. 11, 2021.

International Search Report filed in PCT/US2019/014857 dated Apr. 12, 2019.

* cited by examiner

SYSTEM AND METHOD FOR COOLING OR HEATING A HUMAN BODY PART

BACKGROUND

U.S. Pat. No. 6,183,501 B1 discloses a cooling system having a head and neck device which can be cooled to reduce trauma to the brain. The head device includes panels that each house a cold element to facilitate cooling. The head device secures to the head of an individual and covers over the individual's carotid arteries, which provide blood to the brain. US 2012/0288848 A1 discloses similar devices connected with a pump and cooling fluid source.

The pump and cooling fluid liquid sources have been described as a reservoir surrounded by a cooling unit which is supplied refrigerant from a compressor, for example in U.S. Pat. No. 6,511,502 B2. Ice baths in which ice has been placed into a reservoir of water have also been used as a cooling fluid source.

BRIEF DESCRIPTION

In view of the foregoing, a system for cooling or heating a body part includes at least one bladder, a pump, a heat exchanger, a first fluid line in fluid communication with the heat exchanger and the at least one bladder, a second fluid line in fluid communication with the at least one bladder and the heat exchanger, a main reservoir and a separator. The at least one bladder is configured to be placed on a body part. The heat exchanger is in fluid communication with the pump. The first fluid line is located downstream from the heat exchanger and the second fluid line is located downstream from the at least one bladder when the system is operating to cool or heat the body part. The separator is in fluid communication with the main reservoir and the pump and is located below the main reservoir to receive fluid under the influence of gravity from the main reservoir and to deliver fluid to the pump via gravity.

A unit for providing heated or cooled fluid to an associated bladder to be placed on a body part includes a casing, a pump positioned in the casing, a heat exchanger positioned in the casing, a unit outlet in fluid communication the heat exchanger, a unit inlet in fluid communication with the heat exchanger, a main reservoir positioned in or on the casing and a separator positioned in the casing between and in fluid communication with the main reservoir and the pump. The heat exchanger is in fluid communication with the pump. The unit outlet is positioned with respect to the heat exchanger to receive fluid that has passed through the heat exchanger. The unit inlet is positioned with respect to the heat exchanger to provide fluid to the heat exchanger. The separator is located below the main reservoir to receive fluid under the influence of gravity from the main reservoir. The separator is also located with respect to the pump so as to deliver fluid from the separator to the pump under the influence of gravity. The separator has a volumetric space toward a top of the separator for allowing air bubbles to migrate toward the volumetric space to inhibit air from entering into the pump.

DETAILED DESCRIPTION

Figure 1:
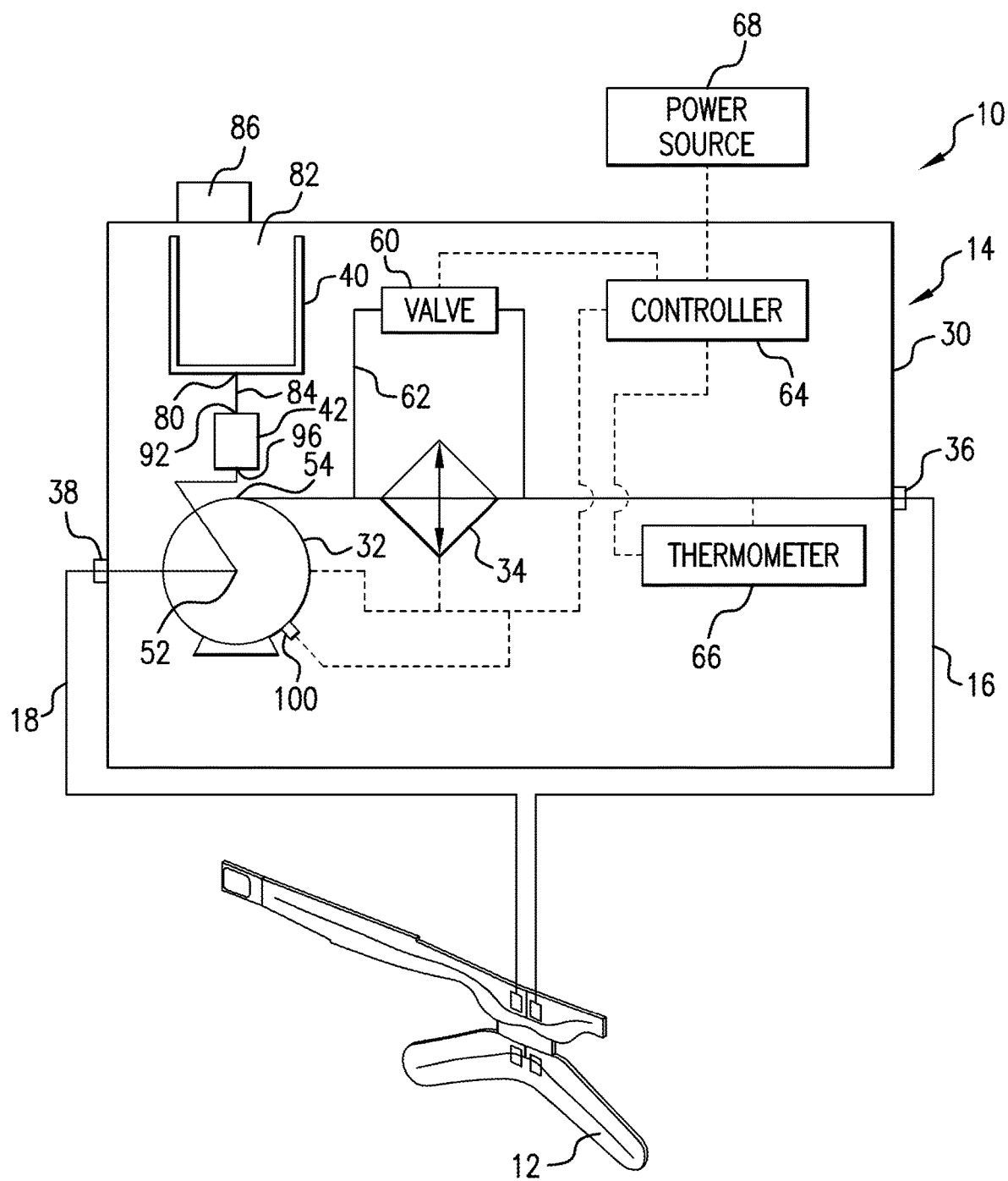
FIG. 1 is a schematic depiction of a system for cooling or heating a body part.

FIG. 1 schematically depicts a system 10 for heating or cooling a body part, such as the head, neck, knee, or other areas of the human body including internal organs such as the brain. The system 10 generally includes at least one bladder 12 that connects to a unit 14, which can be a chiller unit or a heater unit, through a first fluid line 16 and a second fluid line 18. When the system 10 is operating to cool a body part, relatively cooler fluid passes from the unit 14 through the first fluid line 16 toward the bladder 12. The relatively cooler fluid is then warmed when the bladder 12 is brought in proximity to the human body part. Relatively warmer water then exists the bladder 12 and travels toward the unit 14 through the second fluid line 18 to again be cooled for delivery back to the bladder 12. The first and second fluid lines 16, 18 are schematically depicted in FIG. 1 and can include flexible plastic tubing in single or multiple sections having fittings or connectors at each end for connecting with the unit 14 and the bladder 12, respectively.

Figure 2:
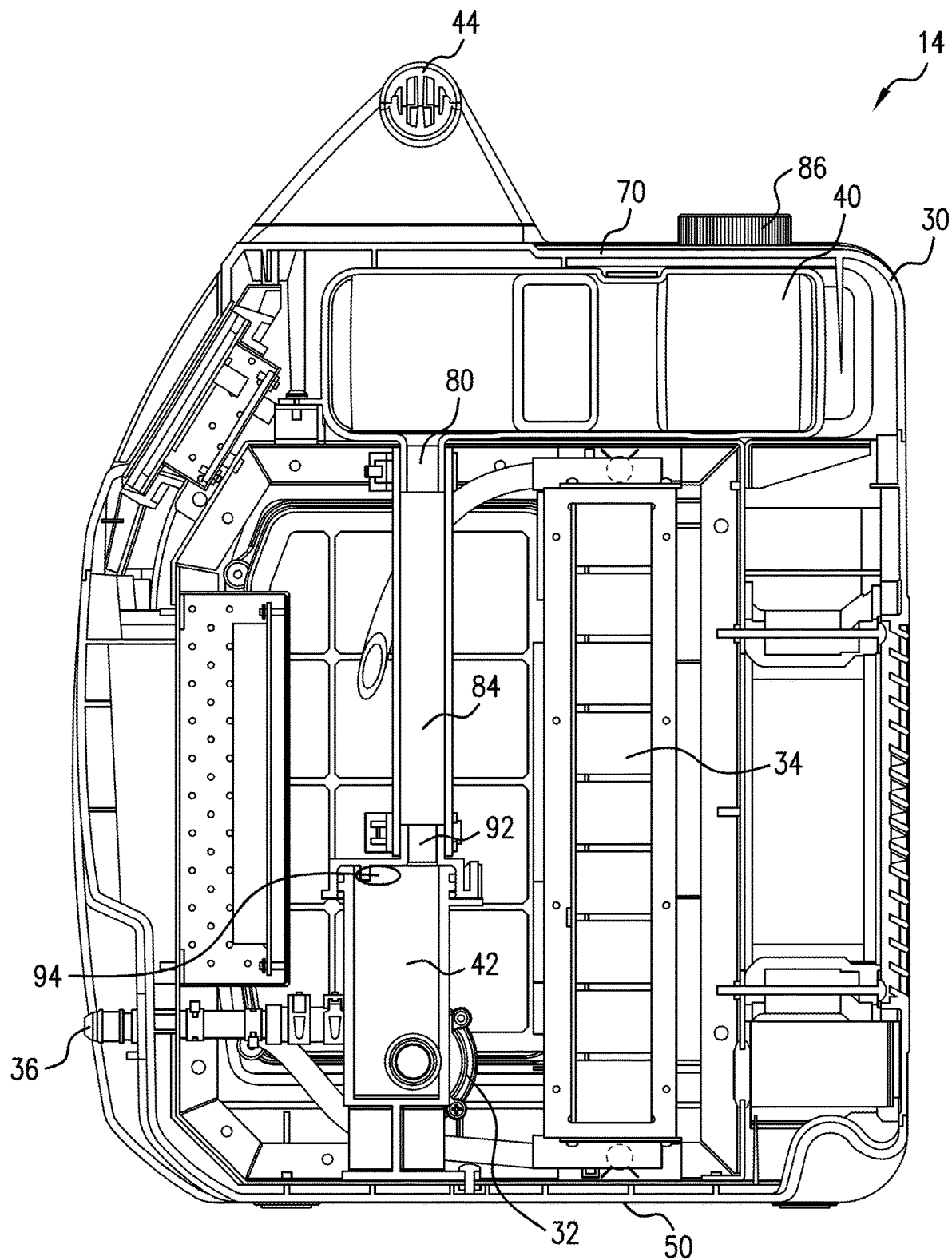
FIG. 2 is a cross-sectional view taken through an example of a unit of the system shown in FIG. 1.

The unit 14 generally includes a casing 30, a pump 32 positioned in the casing 30, a heat exchanger 34 positioned in the casing, a unit outlet 36 in fluid communication with the heat exchanger 34, a unit inlet 38 also in fluid communication with the heat exchanger 34, a main reservoir 40 positioned in or on the casing 30, and a separator 42 positioned in the casing 30 between and in fluid communication with the main reservoir 40 and the pump 32. The unit 22 is designed to be a portable unit that can be easily lifted by a healthy adult. With reference to FIG. 2, the unit 14 can be provided with a handle 44 to allow the unit 14 to be easily carried.

As mentioned above, the casing 30 houses many of the internal components of the unit 14. The casing 30 in the illustrated embodiment is made from a durable plastic material; however, the casing could be made from other material durable materials.

With reference to FIG. 2, the pump 32 is positioned near a lower wall 50 of the casing 30. With reference back to FIG. 1, the pump 32 includes a pump inlet 52 and a pump outlet 54. In the illustrated embodiment, the pump 32 is a centrifugal pump; however, other types of pumps could be used such as positive displacement pumps and the like. The pump 32 draws fluid from the unit inlet 38 through the pump inlet 52 and then out the pump outlet 54.

The heat exchanger 34 is in fluid communication with the pump 32. The heat exchanger 34 is schematically depicted as a cooler in FIG. 2 and will be described as such as part of a cooling system; however, the heat exchanger could also operate as a heater. In the illustrated embodiment, the heat exchanger 34 is positioned downstream from the pump 32 when the system 10 is operating to cool or heat a body part. A valve 60 can be provided downstream from the pump 32. The valve 60 can be opened when it is desirable to have fluid bypass the heat exchanger 34. The valve 60 can be provided on a valve bypass line 62 that connects with the pump 32 upstream from the heat exchanger 34 and then reconnects downstream from the heat exchanger 34. Operation of the valve 60 can be controlled by a controller 64 that is in electrical communication with the valve 60 and a thermometer 66. Opening and closing of the valve 60 can be controlled based on temperature readings provided by the thermometer 66 to the controller 64 so as to provide fluid at a desired temperature exiting the unit 14 through the unit outlet 36.

In operation, when a body part is to be cooled, the bladder 12 is placed on the body part to be cooled, and the unit 14 is turned on so that a power source 68 provides power to the controller 64 and other internal components of the unit 14, such as the pump 32, the heat exchanger 34, the valve 60 and the thermometer 66. The pump 32 pumps fluid so as to exit the pump outlet 54 and travel towards the heat exchanger 34. When the unit 14 is operating as a chiller unit, heat is removed from the fluid resulting in a relatively cooler fluid exiting the heat exchanger 34. The relatively cooler fluid then exits the unit 14 by way of the unit outlet 36 and travels through the first fluid line 16 toward the bladder 12. The relatively cooler fluid travels through the bladder 12 and removes heat from the body part on which the bladder 12 rests. Relatively warmer water then exits the bladder 12 and travels through the second fluid line 18 back toward the pump 32. Fluid within the first fluid line 16, the bladder 12, the second fluid line 18, and traveling through the unit 14 between the unit inlet 38 and the unit outlet 36 operates in a closed circuit in that the circuit is not typically vented or open to ambient. The total volume of fluid passing through the bladder 12, the fluid lines 16, 18, and the unit 14 between the unit inlet 38 and the unit outlet 36 can be referred to as a circuit volume.

The unit 14 further includes the main reservoir 40 located adjacent a top wall 70 of the casing 30. The main reservoir 40 can be positioned in or on the casing 30. The main reservoir 40 has a maximum main reservoir volume at least five times greater than the circuit volume. By only cooling (or heating) the volume of fluid required to provide the desired temperature in the bladder 12 in a closed circuit, i.e., by cooling or heating fluid in the circuit volume, less energy is required to operate the heat exchanger 34 and the pump 32 as compared to if fluid in the main reservoir 40 was also being cooled or heated, which results in a more economical and environmentally friendly unit 14.

The main reservoir 40 includes a main reservoir outlet 80 and a main reservoir inlet 82. The main reservoir 40 is provided inside the casing 30 of the unit 14 in the illustrated embodiment; however, the main reservoir 40 could also be provided on or connected with the casing 30. As mentioned above, the maximum main reservoir volume is much greater than the circuit volume, i.e., the volume of the fluid traveling from the unit 14 to the bladder 12 and then back to the unit 14. The maximum main reservoir volume can be five time or even ten times greater than the circuit volume. In the illustrated embodiment, a main reservoir outlet line 84 connects with the main reservoir outlet 80. A vented cap 86 selectively closes the main reservoir inlet 82. The vented cap 86 is connectable with at least one of the casing 30 and the main reservoir 40 for closing the main reservoir inlet 82. With reference to the embodiment illustrated in FIG. 2, the vented cap 86 threads onto a neck (not visible) that extends through an opening in the top wall 70 of the casing 30.

As illustrated, the separator 42 is in fluid communication with the main reservoir 40 and the pump 32 and is positioned below the main reservoir 40 to receive fluid under the influence of gravity from the main reservoir 40 via the main reservoir outlet line 84. As mentioned above, the pump 32 in the illustrated embodiment is a centrifugal pump. Centrifugal pumps are known to have difficulty priming. Fluid within the main reservoir 40 is fed to the separator 42 via gravity and the separator 42 is located with respect to the pump 32 so as to deliver fluid from the separator 42 to the pump 32 under the influence of gravity. This mitigates issues with regard to priming the pump 32 because the pump 32 is positioned below the main reservoir 40 so that the head pressure of the fluid within the main reservoir 40 forces the fluid through the separator 42 and into the pump inlet 52 to mitigate priming and cavitation issues in the pump 32.

The separator 42 has a separator inlet 92 connected with the main reservoir outlet line 84. The separator 42 has a maximum volume that is smaller than the maximum main reservoir volume. As more clearly seen in FIG. 2, in the illustrated embodiment, the separator 42 also defines a volumetric space 94, which is exaggerated in FIG. 2, inside the separator 42 that is offset from the separator inlet 92 for allowing air bubbles to migrate toward a top of the separator 42 without passing into the main reservoir outlet line 84. This reduces the likelihood of air bubbles exiting the separator 42 through a separator outlet 96 and entering the pump 32, which can result in priming problems for the pump 32, and also reduces the likelihood of air bubbles traveling through the pump 32 and into the fluid lines 16, 18 and the bladder 12. With continued reference to FIG. 2, the separator 42 has a larger cross-sectional area (taken normal to an axis along which the main reservoir outlet line 84 extends) as compared to a cross-sectional area of the main reservoir outlet line 84. This allows for the volumetric space 94 in which the air bubbles can migrate within the separator 42 without having to travel through the more constricted cross-sectional area of the main reservoir outlet line 84. The main reservoir 40 does have the vented cap 86 covering the main reservoir inlet 82, which can allow air to escape from the main reservoir 40. However, air bubbles would have to overcome the pressure of any fluid within the main reservoir 40 pressing against any fluid in the main reservoir outlet line 84 before reaching the vented cap 86.

Fluid passing through the unit 14 from the unit inlet 38, through the pump 32 and the heat exchanger 34 and then through the unit outlet 36, along with traveling through the fluid lines 16, 18 and the bladder 12 will inevitably result in fluid loss due to small leaks or transmissive loss through the bladder 12 and the fluid lines 16, 18 connecting the bladder 12 to the unit 14. This lost fluid is replaced by fluid residing in the separator 42, and the fluid lost in the separator 42 is replaced by fluid that resides within the main reservoir 40. The pump 32, the unit inlet 38, and the separator 42 are configured and positioned in the casing 30 such that the pump 32 primarily draws fluid from the unit inlet 38 and fluid is drawn from the separator 42 by the pump 32 only when fluid is lost from the circuit volume. Again, only fluid passing through the relatively closed circuit between the unit 14 and the bladder 12 is cooled or heated by the heat exchanger 34 and the fluid within the main reservoir 40 typically stays at near ambient temperature.

A sensor 100 is provided to monitor electrical current being drawn by the pump 32. When no more fluid is provided by the separator 42 to the pump 32, the current draw by the pump 32 will spike, and the sensor 100 can detect this state and provide an electrical signal to the controller 64 which can stop delivery of electrical power to the pump 32 and provide an indication to the operator that more fluid is needed in the main reservoir 40.

A system for cooling or heating a body part and a unit for use in such a system have been described above with particularity. Modifications and alterations will occur to those upon reading and understanding the preceding detailed description. The invention, however, is not limited to only the system described above. Instead, the invention is broadly defined by the appended claims and the equivalents thereof. Also, various presently unforeseen or unanticipated alternatives, modifications, variations or improvements may be subsequently made by those skilled in the art which are also intended to be encompassed by the following claims.

The invention claimed is:

1. A system for cooling or heating a body part, the system comprising:
   at least one bladder configured to be placed on a body part;
   a pump including a pump inlet and a pump outlet;
   a heat exchanger in fluid communication with the pump;
   a first fluid line in fluid communication with the heat exchanger and the at least one bladder, the first fluid line being located downstream from the heat exchanger when the system is operating to cool or heat the body part;
   a second fluid line in fluid communication with the at least one bladder and the heat exchanger, the second fluid line being located downstream from the at least one bladder when the system is operating to cool or heat the body part;
   a main reservoir; and
   a separator in fluid communication with the main reservoir and the pump, the separator being located below the main reservoir to receive fluid under the influence of gravity from the main reservoir and to deliver fluid to the pump via gravity and head pressure of the fluid within the main reservoir forces the fluid through the separator and into the pump inlet prior to the fluid from the separator entering either the first fluid line or the second fluid line,
   wherein the main reservoir includes a main reservoir inlet, and the system further includes a vented cap for closing the main reservoir inlet and a main reservoir outlet line connected with an outlet of the main reservoir, wherein the separator has a separator inlet connected with the main reservoir outlet line and defines volumetric space for allowing air bubbles to migrate toward a top of the separator without passing into the main reservoir outlet line, the air bubbles at the top of the separator having to overcome the pressure of any fluid within the main reservoir pressing against any fluid in the main reservoir outlet line before reaching the vented cap.

2. The system of claim 1, wherein the separator has a larger cross-sectional area as compared to a cross-sectional area of the main reservoir outlet line.

3. The system of claim 1, wherein the pump is a centrifugal pump.

4. The system of claim 3, further comprising a sensor configured to detect electrical current being drawn by the pump.

5. The system claim 1, wherein the main reservoir has a maximum main reservoir volume and a total volume of fluid circulating among the at least one bladder, the pump, the first fluid line, the second fluid line and the heat exchanger is a circuit volume, wherein the maximum main reservoir volume is at least 5 times greater than the circuit volume.

6. The system of claim 5, wherein the maximum main reservoir volume is at least 10 times greater than the circuit volume.

7. The system of claim 1, wherein the main reservoir has a maximum main reservoir volume and the separator has a maximum separator volume, which is smaller than the maximum main reservoir volume.

8. The system of claim 1, wherein the pump is upstream from the heat exchanger.

9. The system of claim 1, further comprising a casing, wherein the pump, the heat exchanger, the main reservoir, and the separator are positioned in the casing.

10. The system of claim 1, wherein a total volume of fluid circulating among the at least one bladder, the pump, the first fluid line, the second fluid line and the heat exchanger is a circuit volume,
    wherein the pump is positioned in a casing as part of a unit having a unit inlet in fluid communication with the pump, and the pump, the unit inlet, and the separator are configured and positioned in the casing such that the pump primarily draws fluid from the unit inlet and fluid is drawn from the separator by the pump only when fluid is lost in the circuit volume.

11. A unit for providing heated or cooled fluid to an associated bladder to be placed on a body part, the unit comprising:
    a casing;
    a pump positioned in the casing, the pump including a pump inlet and a pump outlet;
    a heat exchanger positioned in the casing and in fluid communication with the pump;
    a unit outlet in fluid communication with the heat exchanger and positioned with respect to the heat exchanger to receive fluid that has passed through the heat exchanger;
    a unit inlet in fluid communication with the heat exchanger and positioned with respect to the heat exchanger to provide fluid to the heat exchanger;
    a main reservoir positioned in or on the casing, the main reservoir including a main reservoir outlet;
    a main reservoir outlet line connected with the main reservoir outlet;
    a separator having a separator inlet connected with the main reservoir outlet line and a separator outlet, the separator being positioned in the casing between and in fluid communication with the main reservoir outlet and the pump inlet, the separator being located below the main reservoir to receive fluid under the influence of gravity from the main reservoir, the separator being located with respect to the pump so as to deliver fluid from the separator to the pump under the influence of gravity via a fluid line connecting the separator outlet to the pump inlet such that the fluid from the separator does not exit the casing before entering the pump, wherein the separator is positioned in the casing such that fluid is drawn from the separator into the pump inlet only when fluid is lost in a circuit between the unit inlet and the unit outlet.

12. The unit of claim 11, wherein the separator defines volumetric space for allowing air bubbles to migrate toward a top of the separator without passing into the main reservoir outlet line.

13. The unit of claim 12, wherein the main reservoir has a maximum main reservoir volume and the separator has a maximum separator volume, which is smaller than the maximum main reservoir volume.

14. The unit of claim 13, wherein the separator has a larger cross-sectional area as compared to a cross-sectional area of the main reservoir outlet line.

15. The unit of claim 14, further comprising a sensor configured to detect electrical current being drawn by the pump, and the pump is a centrifugal pump.

16. The unit of claim 15, wherein the pump is upstream from the heat exchanger.

* * * * *